United States Patent [19]

Sanese

[11] Patent Number: 5,368,569
[45] Date of Patent: Nov. 29, 1994

[54] IRRIGATION SYSTEM FOR PREVENTING CONTAMINATION AND REDUCING THE RISK OF PATIENT HYPOTHERMIA

[75] Inventor: Christopher N. Sanese, Columbus, Ohio

[73] Assignee: Sanese Medical Corporation, Columbus, Ohio

[21] Appl. No.: 111,149

[22] Filed: Aug. 18, 1993

[51] Int. Cl.⁵ .................... A61F 7/12; A61M 37/00
[52] U.S. Cl. ..................... 604/113; 604/132; 604/141; 128/DIG. 12
[58] Field of Search ............... 604/113, 131, 132, 141, 604/142, 146, 153; 128/DIG. 12; 222/95

[56] References Cited

U.S. PATENT DOCUMENTS

| | | | |
|---|---|---|---|
| 817,054 | 4/1906 | Gay | 604/141 |
| 1,819,807 | 8/1931 | Baysinger | 604/113 |
| 2,766,907 | 10/1956 | Wallace, Jr. | 128/DIG. 12 |
| 3,153,414 | 10/1964 | Beall et al. | 604/142 |
| 3,578,774 | 5/1971 | McDonald, Jr. | |
| 3,838,794 | 10/1974 | Cogley et al. | 604/141 |
| 3,986,508 | 10/1976 | Barrington | 604/905 |
| 4,090,514 | 5/1978 | Hinck et al. | 128/DIG. 12 |
| 4,369,785 | 1/1983 | Rehkopf et al. | |
| 4,507,116 | 3/1985 | Leibinsohn | 128/DIG. 12 |
| 4,539,005 | 9/1985 | Greenblatt | 604/141 |
| 4,551,136 | 11/1985 | Mandl | 604/141 |
| 4,561,431 | 12/1985 | Atkinson | |
| 4,604,089 | 8/1986 | Santangelo et al. | |
| 4,613,327 | 9/1986 | Tegrarian et al. | 128/DIG. 12 |
| 4,637,814 | 1/1987 | Leiboff | |
| 4,657,160 | 4/1987 | Woods et al. | 604/141 |
| 4,669,453 | 6/1987 | Atkinson et al. | |
| 4,713,051 | 12/1987 | Steppe et al. | |
| 4,735,613 | 4/1988 | Bellin et al. | 604/141 |
| 4,781,687 | 11/1988 | Wall | |
| 4,808,159 | 2/1989 | Wilson | 604/113 |
| 5,011,471 | 4/1991 | Miyazaki et al. | |
| 5,019,038 | 5/1991 | Linden | |
| 5,053,002 | 10/1991 | Barlow | |
| 5,053,011 | 10/1991 | Strobel et al. | 604/141 |
| 5,098,387 | 3/1992 | Wiest et al. | |
| 5,106,366 | 4/1992 | Steppe | |
| 5,125,900 | 6/1992 | Teves | 604/142 |
| 5,176,629 | 1/1993 | Kullas et al. | |
| 5,178,606 | 1/1993 | Ognier et al. | |
| 5,261,255 | 11/1993 | Coelho et al. | 604/113 |

Primary Examiner—C. Fred Rosenbaum
Assistant Examiner—Frank Wilkens, III
Attorney, Agent, or Firm—Dinsmore & Shohl

[57] ABSTRACT

The invention concerns a surgical apparatus for irrigating an operative site during endoscopic surgery. The apparatus comprises a reservoir of irrigation fluid contained within an air actuated pouch, a pump for inflating the pouch so that the reservoir is compressed, pressure control means, a microprocessor for operating the system, heating panels contained within the pouch for providing heated irrigation fluid, and a nozzle and tube for delivering the irrigation fluid to an operative site. The apparatus also provides a stick fitting for attaching tubing to the fluid reservoir. In addition to the stick fitting, the apparatus provides a locking receiver system for insuring that the stick fitting will not disengage during use.

21 Claims, 6 Drawing Sheets

IRRIGATION SYSTEM FOR PREVENTING CONTAMINATION AND REDUCING THE RISK OF PATIENT HYPOTHERMIA

FIELD OF THE INVENTION

This invention generally relates to the field of irrigation delivery systems, and, more particularly, to an improved irrigation delivery system that heats the irrigation fluid, provides the irrigation fluid under higher pressures, and prevents contamination of the sterile irrigation fluid.

BACKGROUND OF THE INVENTION

Irrigation of a surgical or operative site accomplishes three goals. First, flushing the site with fluid cleans the area of blood and tissue providing a surgeon with an improved view. Secondly, the fluid functions as a medium for removal of blood and debris during aspiration of the operative site. Thirdly, pressurized irrigant is used to gently separate anatomical structures for accessing adjacent structures. High pressure irrigant is desired for use in laser surgery, well known systems cannot provide sufficient pressure for that use.

Irrigation delivery systems typically include measurement and control instruments to adjust flow rates, a reservoir for the sterile irrigation fluid, a pump or other flow producing means, a flexible sterile conduit, and an operative instrument for discharging fluid to an operative site.

Well known irrigation systems include gravity systems, pressurized gas systems, various mechanical pump designs, and pressure vessel compression systems. The gravity systems usually suspend the irrigation fluid at an elevated height to produce fluid flow. A problem associated with gravity systems is that, typically, these systems cannot achieve high flow rates.

Pressurized gas systems pump gas into a sterile fluid container and force the fluid out of the container, through a conduit and into an operative instrument for delivery to the operative site. A problem with gas systems is that the gas contacts the sterile fluid and may introduce contaminants into the fluid. Another problem with these systems is cross-flow contamination. Cross-flow contamination occurs when contaminated fluid at the operative site backflows into the sterile conduit.

Mechanical pumps include complex pneumatic, systolic, and peristaltic pumps as well as disposable sterile pumps. Pumps are generally undesirable because they are not self contained, operate at high noise levels, and contaminate the sterile irrigation fluid.

A pressure vessel system utilizes a rigid housing for holding a flexible fluid bag. Flow is achieved pressurizing the area within the housing with either gas or fluid such that the bag is compressed. Problems associated with these systems are a small irrigant capacity and contamination at the interfaces between the housing and the tubing connected to the housing. In addition, this type of system is often undesirable because it utilizes a hospital's gas supply line which limits the system's mobility and makes the gas supply line unavailable for other uses. It is desirable to have irrigation fluid preheated to prevent patient hypothermia, however, there are frequently pre-surgery delays during which the fluid cools. Consequently, a system capable of maintaining fluid at its preheated temperature is desired. One system that has attempted to solve this problem is a heated water bath where the bags of irrigant are immersed in the bath and fluid is pumped from the bag up through the control system. However, disadvantages associated with this system are that the system is not self contained, is cumbersome, and is inconvenient. Another system provides a sleeve having a heating element that slides over a portion of the tubing so that fluid is heated as it travels through that portion of the tubing. Problems associated with this system are that the preheated temperature is not maintained and the sleeve is inconvenient and time consuming to use.

Another disadvantage associated with existing irrigation systems is that changing an empty reservoir of fluid is time consuming and inconvenient so that it often interrupts surgery.

It is the object of this invention to provide a simple, self-contained, mobile irrigation system which is capable of providing highly pressurized irrigant; the elimination of irrigant contamination; a large volume of irrigant; its own gas supply through a self-contained method of pressurization; warm irrigant to the operative site; irrigant at a pressure which is sufficient for use in laser surgery; convenient and quick changing of irrigation bags; and quiet operation at less than 40 dBA.

SUMMARY OF THE INVENTION

Accordingly, the irrigation system of this invention meets the above-stated objectives and is particularly designed for reducing the risk of patient hypothermia and preventing irrigation fluid contamination. The present invention is adapted to provide improved, adjustable flow rates for use during laser surgery which requires higher fluid pressure to create a fluid film barrier to control laser penetration depth.

The irrigation system is self contained and provides heated irrigant while eliminating contamination of the sterile system. The system utilizes an air actuated pouch to compress a flexible fluid reservoir. Heating panels with embedded thermistors are located within the pouch to maintain the temperature of the preheated fluid reservoir. The pouch contains an inflatable air bladder that compresses the reservoir and discharges fluid from the reservoir when the bladder is inflated. The fluid is discharged through a tube and a nozzle to an operative site. A support bag surrounds the reservoir allowing the reservoir to be quickly inserted into the pouch so that the surgical procedure is not interrupted when a new reservoir is required. In addition, the support bag prevents the reservoir from being pinched during inflation of the pouch.

The pouch is connected to a rigid housing which contains a pump and a control system. The rigid housing has heat and pressure adjustment controls and a display for giving pressure and temperature information. The system operates at reduced noise levels, below about 40dBA, due to the positioning of the pump within the housing. By employing a pump, the system operates independently of the hospital gas lines; thus, making the gas lines available for other uses. Another advantage of the present invention is that it is lightweight and can be attached to an intravenous ("IV") pole where it is not underfoot and user adjustments can be easily made.

The control system utilizes a microcontroller, a pump, a pressure sensor, and a solenoid valve to regulate fluid pressure. In addition, the control system reads and displays the pressure and temperature. Positive pressure is maintained on the fluid for preventing cross-flow contamination of the system.

DETAILED DESCRIPTION OF THE INVENTION

Figure 1:
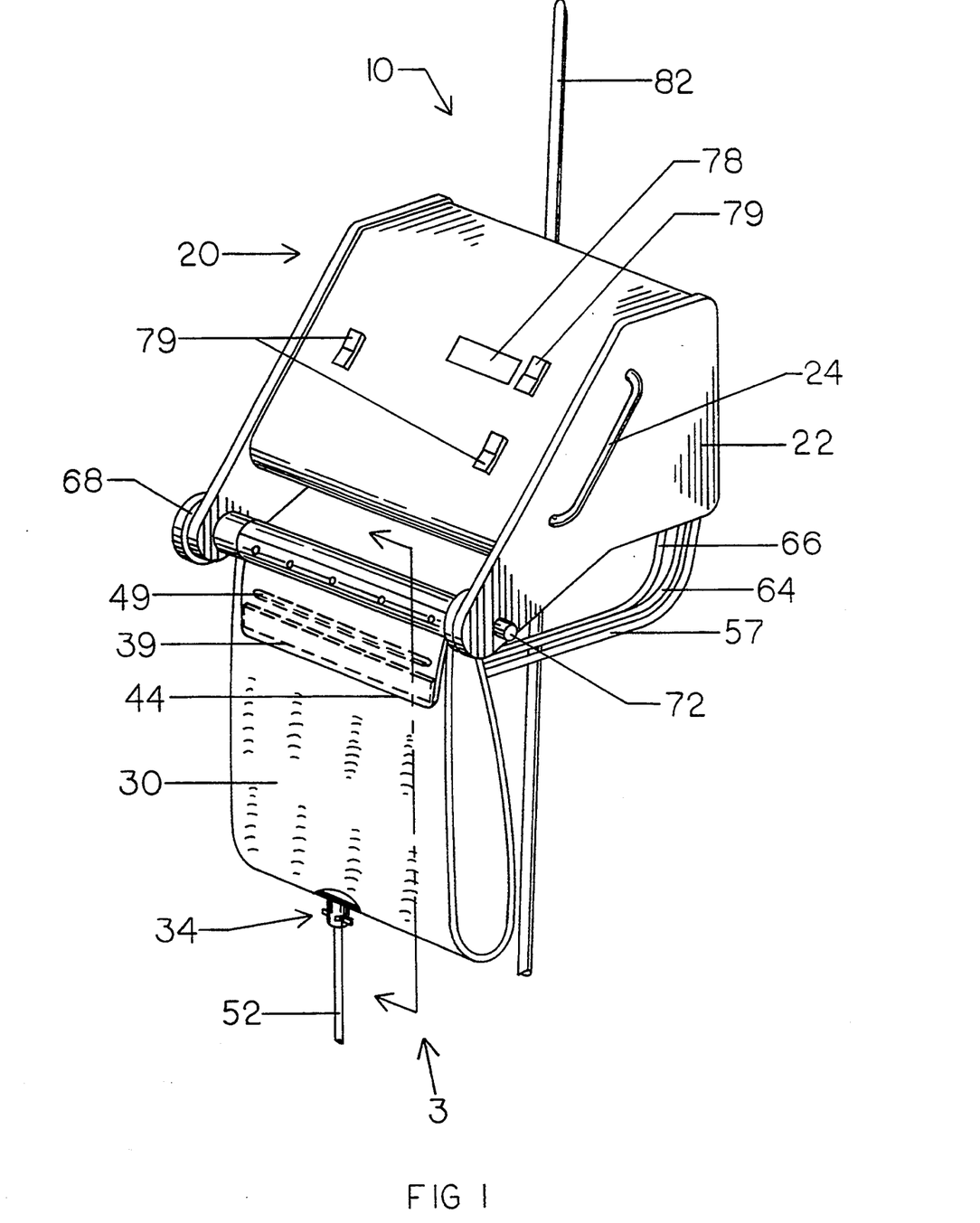
FIG. 1 is a perspective view of the irrigation system attached to an IV pole.

Referring to the drawings, FIG. 1 illustrates a surgical irrigation system (10) that reduces the risk of patient hypothermia and prevents fluid contamination during surgery. The irrigation system is lightweight and self contained so that it is quiet, hangs from a standard IV pole (82), and operates independently of hospital gas lines (not shown). Irrigation system (10) comprises a control system (20) and an air actuated pouch (30). Air actuated pouch (30) is particularly designed for use as part of an irrigation system, but could be used in other applications requiring pressurized fluid.

Figure 2:
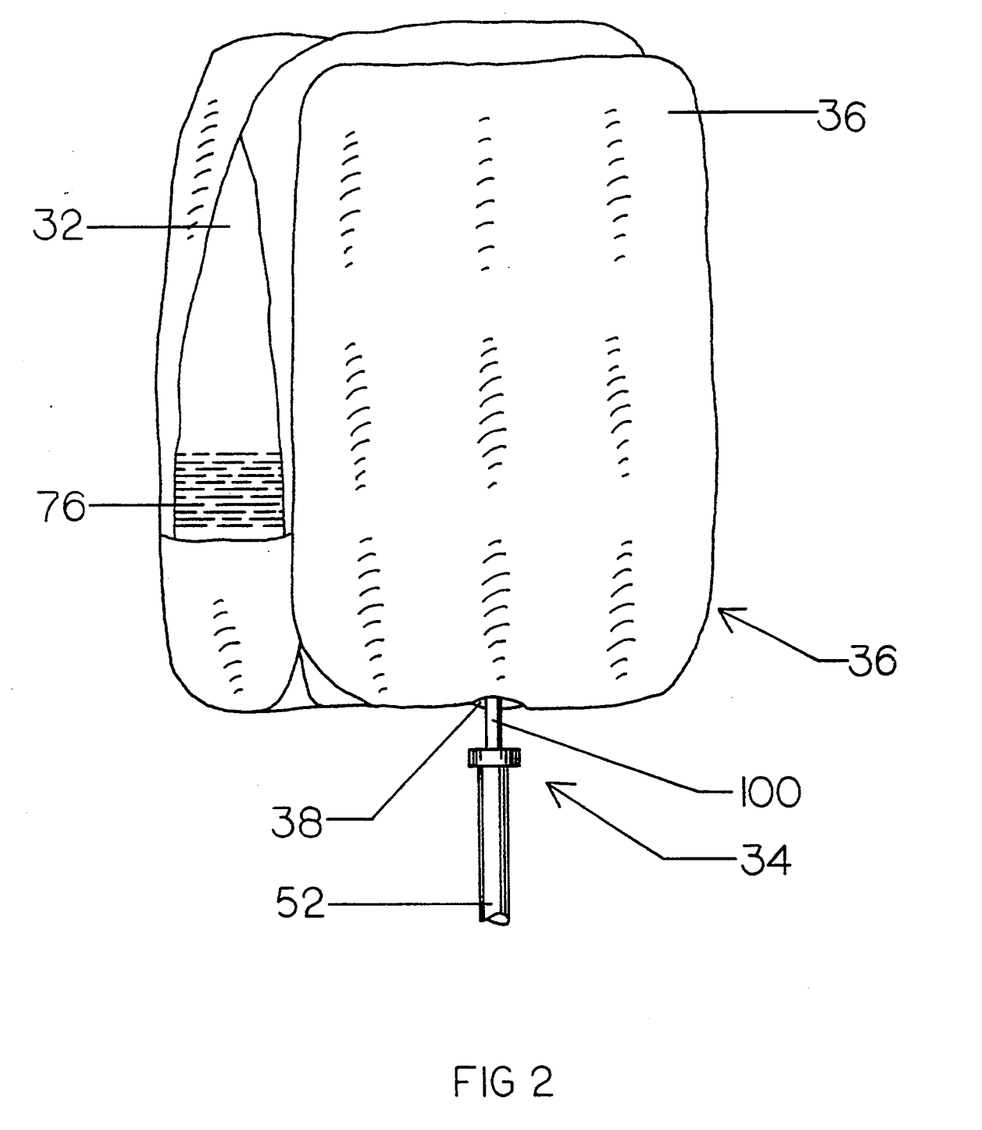
FIG. 2 is a perspective view of the support bag.
Figure 6:
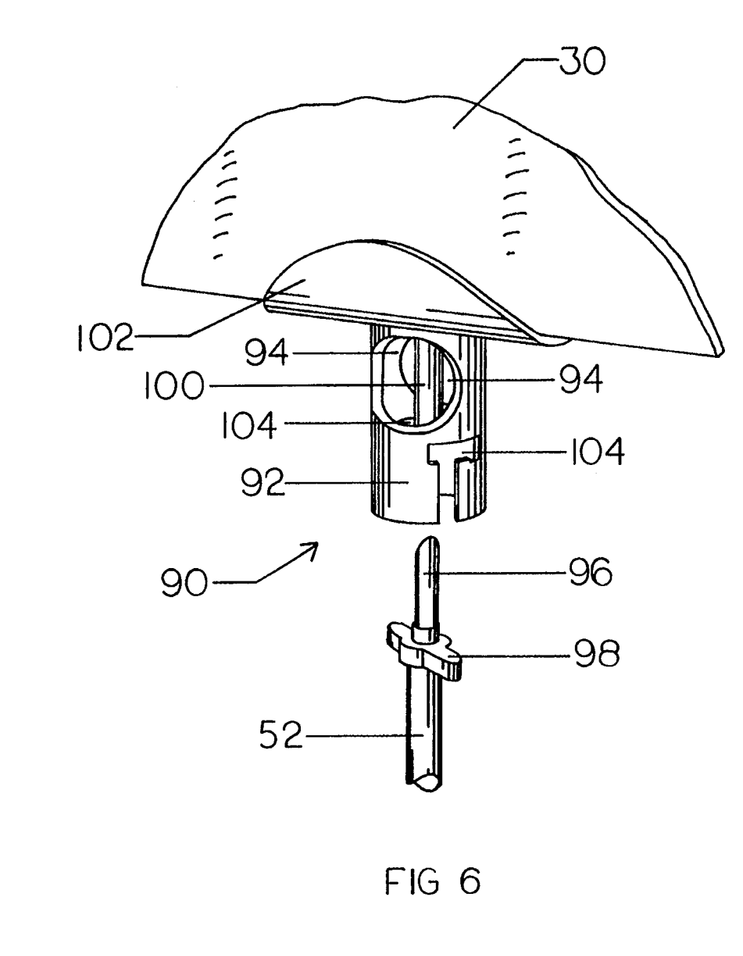
FIG. 6 is a close up view of a disengaged locking piercing pin and receiver system.
Figure 6A:
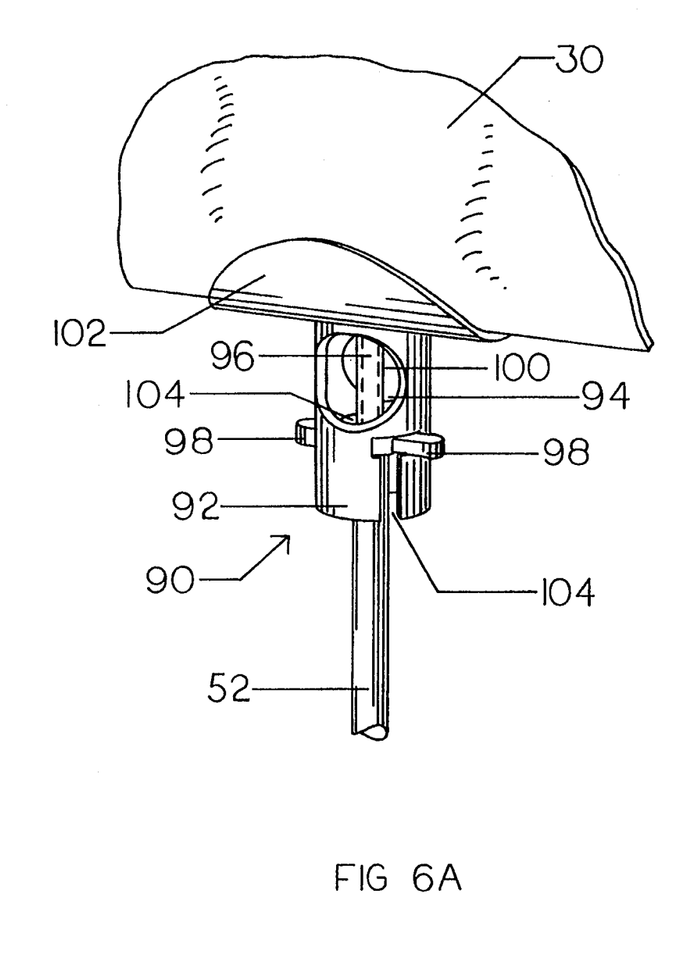
FIG. 6A is a close up view of the locking piercing pin and receiver system of FIG. 6 in the engaged position.

As shown in FIG. 2, irrigation fluid (76) is contained in a flexible fluid reservoir (32). The reservoir is a standard three liter or a one liter bag of preheated, sterile irrigation fluid. However, three liter bags are more convenient because less frequent bag changing is required. Reservoir (32) further comprises a receiver (100) portion of a standard stick fitting (34) for discharging fluid from the bag without introducing contaminants into the fluid. A piercing pin (96) attached to a tube (52) is inserted into receiver (100) for discharging the fluid. A locking piercing pin and receiver system is illustrated in FIG. 6 and FIG. 6A and discussed in detail below. Reservoir (32) is sterilized and packaged so as to maintain sterility until the fluid is discharged to an operative site.

Reservoir (32) fits within a support bag (36) so that reservoir (32) can be easily and quickly inserted into pouch (30) and to prevent pinching of reservoir (32) during inflation. An opening (38) in the bottom of support bag (36) is aligned with receiver (100).

Figure 3:
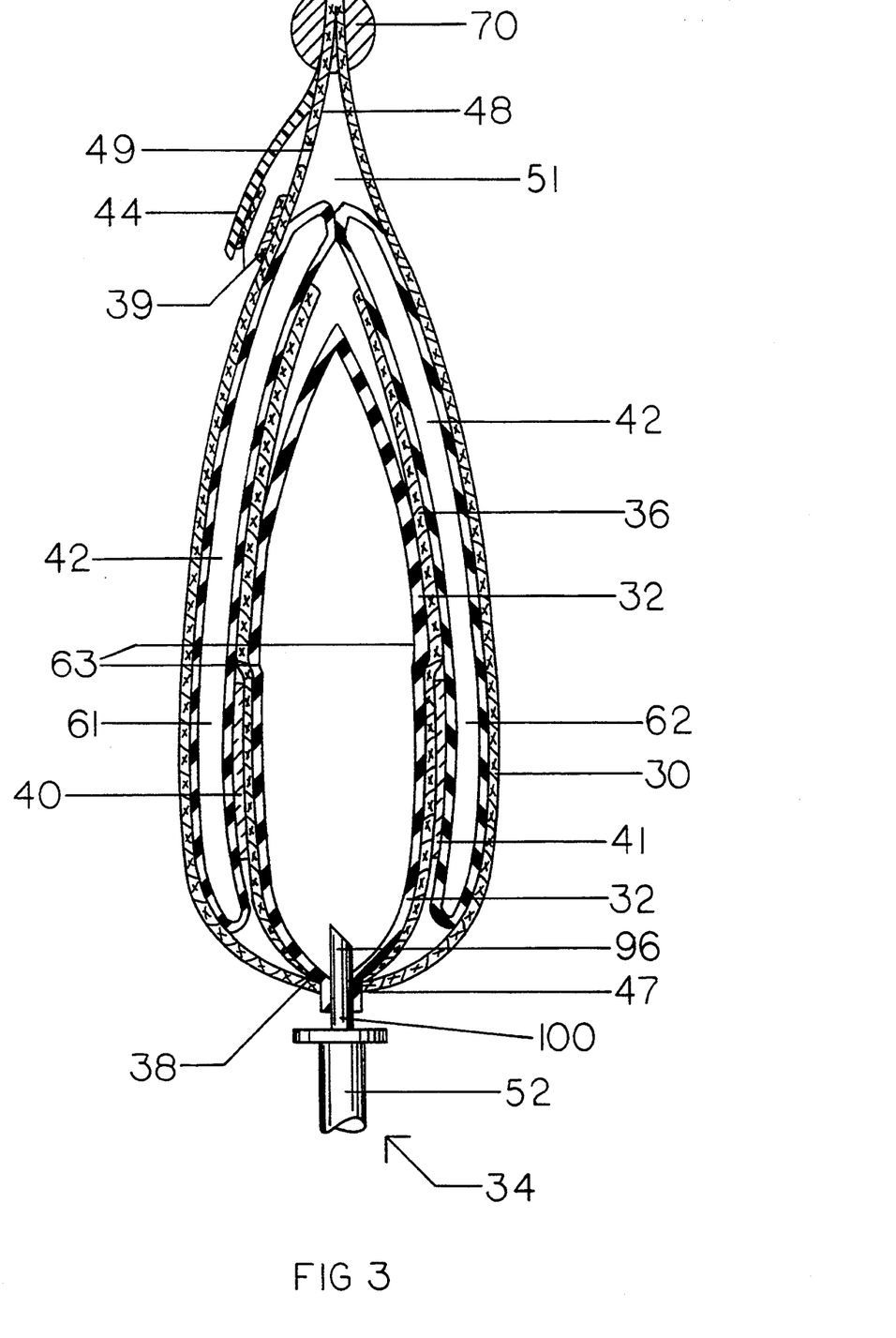
FIG. 3 is a sectional view of the pouch taken along line 3—3 of FIG. 1.

As shown in FIG. 3, support bag (36) fits within pouch (30). Pouch (30) has an inside cavity (51) for containing support bag (36), an interior surface (48), a mouth (49), at least one air bladder (42) for compressing reservoir (32), at least one flexible heating panel (40) for maintaining the temperature of the preheated irrigation fluid, a receptacle (47) for aligning with stick fitting (34) and support bag opening (38), a cover flap (44) for sealing reservoir (32) within the pouch, and fastening means (39) on cover flap (44) and pouch (30) for securely closing pouch (30).

Figure 4:
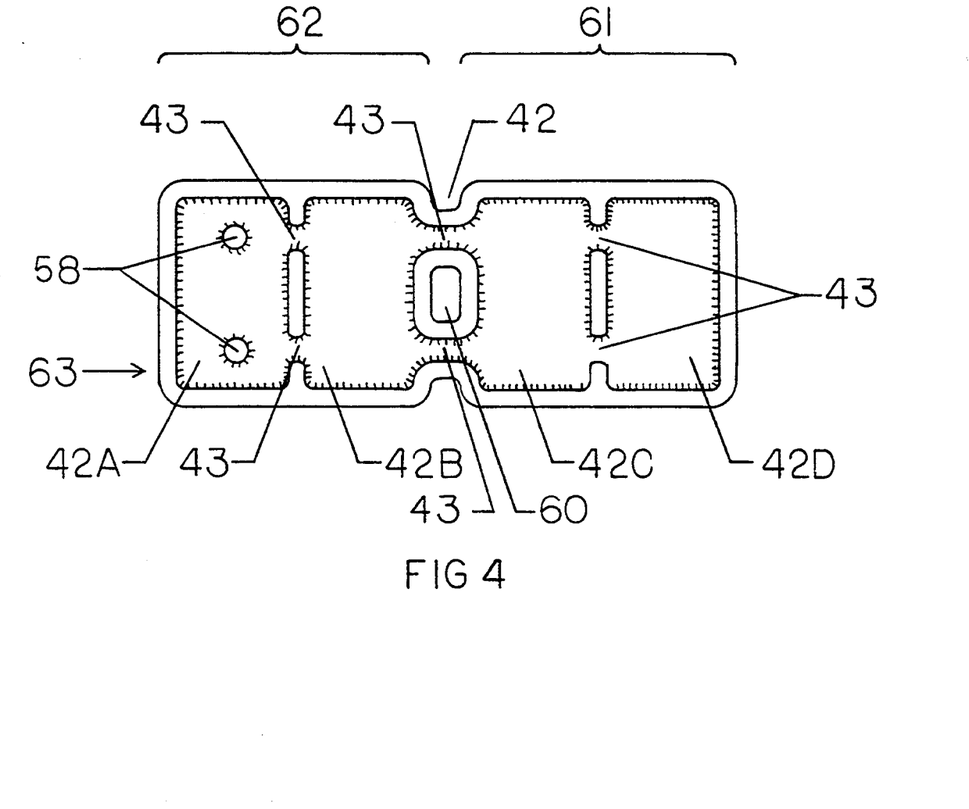
FIG. 4 is a plan view of a laid out air bladder.

Pouch (30) contains at least one air bladder (42) secured to pouch interior surface (48) of pouch inside cavity (51). Although various air bladder designs are possible, the preferred embodiment of the air bladder is shown in FIG. 4. Air bladder (42) has four chambers (42A-D). As chambers (42A-D) are inflated, reservoir (32) is compressed such that fluid is pressurized and discharged through stick fitting (34). The number of chambers (42A-D) are based on the strength of the seams of the bladder (42), and one skilled in the art may readily determine the number of chambers required.

Suitable air bladders (42) are urethane film sheets that have nylon laminated to the urethane to provide strength and puncture resistance. The laminate is RF welded so that chambers (42A-D) are formed as shown in FIG. 4. The bladder (42) has an opening (60) for aligning with receiver (100) of fluid reservoir (32). Bladder (42) may be attached to pouch interior surface (48) by various means, however, a suitable method is by sewing the bladder (42) onto pouch interior surface (48).

Chambers (42A-D) are connected by channels (43) such that they can be evenly and simultaneously inflated, and thus, provide even distribution of pressure on reservoir (32). Channels (43) are formed by RF welding portions of the laminate. Connector locations (58) are RF welded circles for connections of an air feed line (57) and an air sensor line (64) from the control system (20) to inflate bladder (42). Although FIG. 3 shows a single air bladder (42) having a front portion (61) and a back portion (62), suitable designs having two, four, six or more separate bladders are possible. Support bag (36) and pouch (30) can be made out of any inelastic fabric, however, reinforced nylon material provides easy and quick insertion of the support bag into the pouch for easy reservoir changing.

Heating panels (40, 41) are disposed on bladder (42) such that one panel (40) is located on front portion (61) and the other panel (41) is located on back portion (62). Alternatively, heating panels (40, 41) may be attached to support bag (36) (not shown) or to pouch inside cavity (51) (not shown) if desired. A desirable temperature range of the heating panels (40, 41) is about 85° F. to about 115° F. However, the fluid temperature is usually maintained at about 98° F. to about 100° F. to reduce the risk of patient hypothermia.

A suitable heating panel (40, 41) is constructed of mylar film having thermistors (not shown) embedded in the panels for regulating the temperature of the heating panels. Heating panels (40, 41) may be attached to bladder (42) (or other structures) by various means, however, a suitable means is by sewing. Heating panels (40, 41) are connected to control system (20) by heater cable (66).

Although there are several suitable methods for securely fastening pouch (30), a desirable method is shown in FIG. 1 and FIG. 3 where fastening means (39) is high strength velcro strips that are disposed on cover flap (44) and pouch (30).

Figure 5:
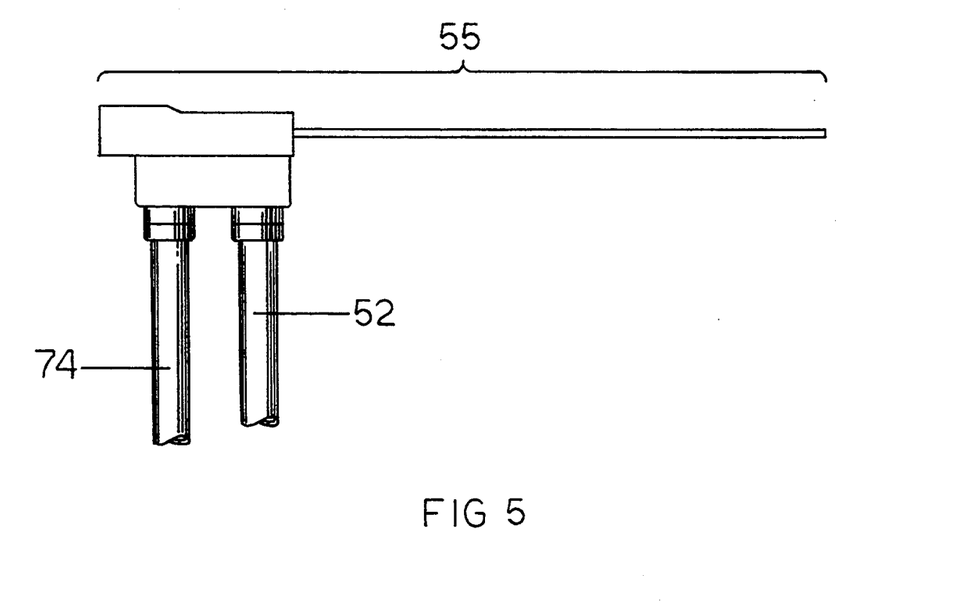
FIG. 5 is a perspective view of the operative instrument.

As shown in FIG. 1 and FIG. 5, irrigation system (10) further comprises an irrigation nozzle (55) for discharging irrigation fluid to an operative site (not shown), a flexible tube (52) having a piercing pin (96) at an end opposite nozzle (55) for connecting the nozzle to reservoir (32) by inserting the pin into receiver (100) and piercing the reservoir, and a vacuum line (74) for connecting to a hospital aspiration system.

A preferred embodiment is shown in FIG. 6 and FIG. 6A that prevents piercing pin (96) from being pushed or knocked out of receiver (100). A locking piercing pin and receiver system (90) is employed to prevent tubing (52) from being pushed out of reservoir (32) by either pressure or reservoir movement during inflation, or by accidental movement of reservoir (32). Locking piercing pin and receiver system (90) comprises a locking receiver (92) attached to pouch (30) and a locking piercing pin (96) attached to tubing (52). Locking receiver (92) has a receiver plate (102) for attaching to pouch (30) and surrounding pouch receptacle (47). Locking receiver (92) extends from plate (102) surrounding stick fitting receiver (100). Locking piercing pin (96) is a standard stickfitting piercing pin, but has locking lugs (98) attached to tubing (52).

To connect tubing (52) to fluid reservoir (32), a user grasps grip openings (94) which are located on locking receiver (92) and inserts piercing pin (96) into receiver (100). Locking lugs (98) should be aligned with locking lug openings (104) so that lugs (98) slip into openings (104) as piercing pin (96) inserts into receiver (100). Locking lugs (98) are then turned so that they are locked into opening (104) and piercing pin (96) can not be inadvertently removed from receiver (100).

Figure 7:
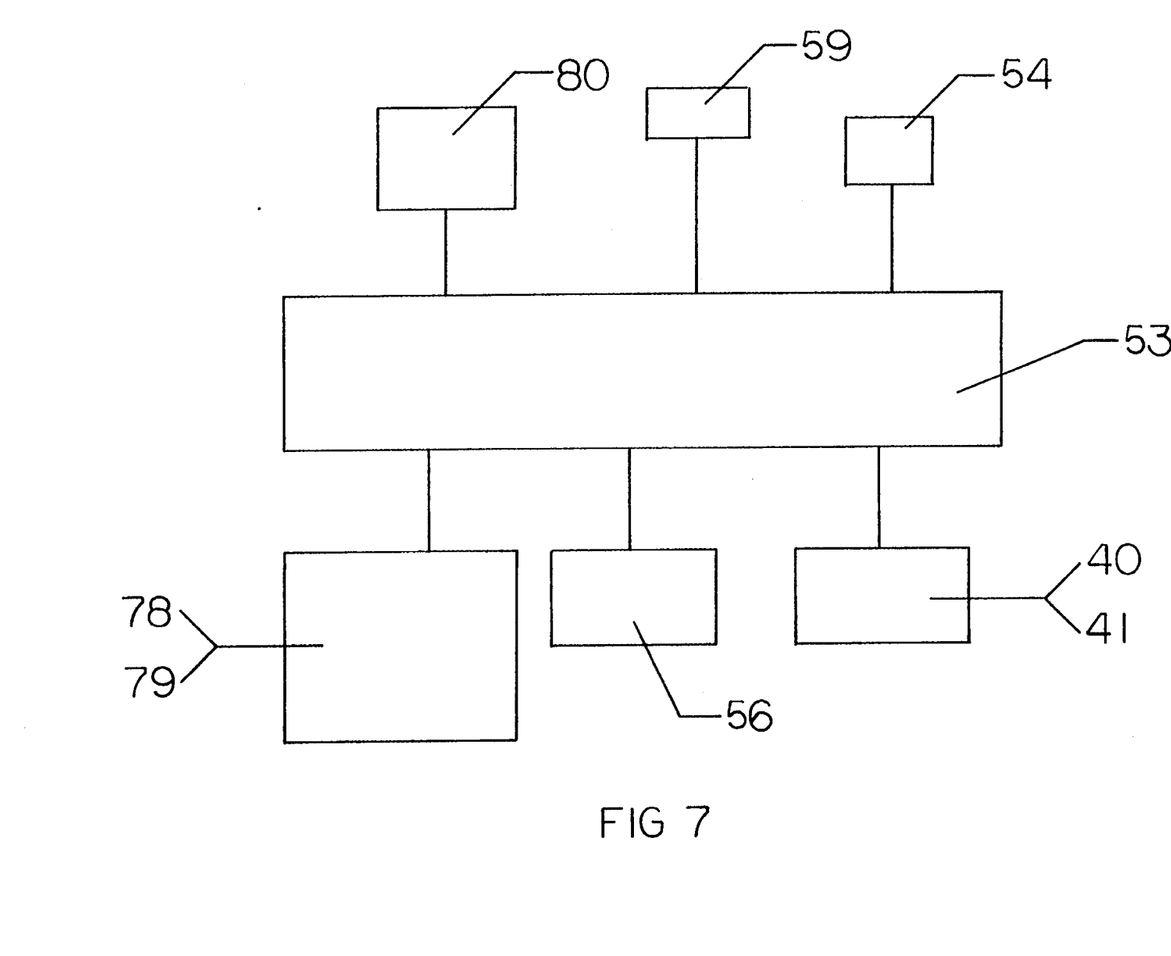
FIG. 7 is a schematic diagram illustrating the electrical connections.

Control system (20) is located in a rigid housing (22) having handles (24) located on the housing for easy transport. As shown in FIG. 7, control system (20) is a microcontroller (53) which is electrically connected to a pump (54) for inflating the pouch, a pressure sensor (56) for monitoring pressure, a solenoid valve (59) for regulating pressure, thermistors in the heating panels (40, 41) for regulating temperature, a power supply (80), a display (78) for displaying temperature and pressure readings, and adjustment switches (80) for adjusting pressure and temperature. The system pressure is adjustable from about 0 mm Hg to about 800 mm Hg. A suitable pressure sensor is a Honeywell Micro Switch 180PC series solid state or a Motorola MPX5100 series piezoresistive transducer. A Medo pump is desirable because it is faster than other models and capable of working with simpler control systems.

As illustrated in FIG. 1, FIG. 3, FIG. 5 and FIG. 7, microcontroller (53) activates pump (54) and regulates solenoid valve (59) which allows air to be pumped through air feed line (57) extending from pump (54) to air bladder (42) in pouch (30). As bladder (42) inflates, it compresses reservoir (32) and sterile irrigant (76) is discharged under pressure through stick fitting (34), into tube (52), and into nozzle (51) to be delivered to the operative site. An air sensor line (64) extends from pressure sensor (56) to air bladder (42) for monitoring pressure. Microcontroller (52) switches heating panels (40, 41) on and off through heater cable (66).

Various means of attaching pouch (30) to said control system (20) exist for suspending the unit from an I.V. pole; however, a suitable mechanism is shown in FIG. 1. Pouch (30) is inserted into take up reel (70). Take up wheel (68) is turned so that pouch (30) is secured around reel (70). Reel lock (72) is secured so that gravity will not cause pouch (30) to unwind from reel (70).

While a particular embodiment of the present invention has been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A surgical apparatus, comprising:
a flexible pouch having a substantially enclosed inside cavity defined by at least one flexible wall for containing and substantially fully enclosing at least bottom and side surfaces of a disposable flexible fluid reservoir;
said pouch further comprising a second inflatable cavity exterior to said inside cavity for receiving a pressurized fluid and applying a compressive force against said at least one flexible wall of said inside cavity.

2. The apparatus of claim 1 wherein said second cavity further comprises a plurality of chambers, said chambers being interconnected by channels for even inflation of said second cavity.

3. The apparatus of claim 2 further comprising a support bag for containing said reservoir, said support bag containing said reservoir is insertable into said pouch inside cavity.

4. The apparatus of claim 1, further comprising a heater located in said pouch for heating said reservoir.

5. The apparatus of claim 4 wherein said heater comprises at least one heating panel located within said pouch inside cavity.

6. The apparatus of claim 5 wherein said heater comprises two said heating panels.

7. The apparatus of claim 5 wherein said at least one heating panel being attached to a surface of said pouch inside cavity.

8. The apparatus of claim 5 wherein said heater being attached to said second cavity.

9. The apparatus of claim 5 wherein said heater being attached to an interior surface of said support bag.

10. A surgical apparatus for preventing contamination of irrigation fluid during surgery, comprising:
a flexible pouch having a substantially enclosed inside cavity defined by at least one flexible wall for containing and substantially fully enclosing at least bottom and side surfaces of a disposable flexible fluid reservoir, and a second inflatable cavity external to said inside cavity for receiving a pressurized fluid and applying a compressive force against said at least one flexible wall of said inside cavity;
a pump for inflating said second cavity;
pressure control means for regulating said pressurized fluid; and
a heater for heating said fluid.

11. The surgical apparatus of claim 10 wherein said second cavity further comprises a plurality of chambers, said chambers being interconnected by channels for even inflation of said second cavity.

12. The surgical apparatus of claim 10 further comprising a support bag for containing said reservoir, said support bag containing said reservoir is insertable into said pouch.

13. The surgical apparatus of claim 10 wherein said heater comprises at least one heating panel located within said pouch inside cavity.

14. The surgical apparatus of claim 10 further comprising a nozzle and a flexible tube attached to said nozzle for discharging said fluid from said reservoir to the surgical site.

15. The surgical apparatus of claim 14 wherein said pouch further comprises:
a locking receiver for preventing said flexible tube from disengaging said fluid reservoir; and
said flexible tube comprises a piercing pin located at an end of said tube for penetrating said reservoir and locking lugs located adjacent said piercing pin for fitting into said locking receiver.

16. The surgical apparatus of claim 10 wherein said pressure control means comprises a solenoid valve.

17. The surgical apparatus of claim 13 wherein said at least one heating panel further comprises thermistors for maintaining said fluid at temperature between about 85° F. and about 115° F.

18. The surgical apparatus of claim 10 wherein said pump operates at a noise level of less than about 40 dBA.

19. The surgical apparatus of claim 18 further comprising a nozzle and a flexible tube attached to said nozzle for discharging said fluid from said reservoir to the surgical site.

20. The surgical apparatus of claim 19 wherein said pouch further comprises:

a locking receiver for preventing said flexible tube from disengaging said fluid reservoir; and said flexible tube comprises a piercing pin located at an end of said tube for penetrating said reservoir and locking lugs located adjacent said piercing pin for fitting into said locking receiver.

21. A surgical apparatus for reducing the risk patient hypothermia and contamination of irrigation fluid during surgery, comprising:

a flexible pouch having a substantially enclosed inside cavity defined by at least one flexible wall for containing and substantially fully enclosing at least the bottom and side surfaces of a disposable flexible fluid reservoir, said reservoir having a stick fitting secured to said bottom through which said fluid is discharged, a second inflatable cavity external to said inside cavity for receiving a pressurized fluid and applying a compressive force against said at least one flexible wall of said inside cavity, said second cavity having a plurality of chambers, said chambers being interconnected by channels for even inflation of said second cavity, a heater having at least one heating panel within said pouch inside cavity for heating said fluid;

a support bag for containing said reservoir, said support bag being insertable into said pouch;

a pump for inflating said second cavity;

a solenoid valve for regulating said pressurized fluid;

said at least one heating panel further comprising thermistors for maintaining said fluid at a temperature between about 85° F. and about 115° F.

* * * * *